(12) United States Patent
Mourelle Mancini et al.

(10) Patent No.: US 7,001,910 B1
(45) Date of Patent: Feb. 21, 2006

(54) THIAZOLIDINEDIONE DERIVATIVES AS ANTIDIABETIC AGENTS

(75) Inventors: Marisabel Mourelle Mancini, Barcelona (ES); Juan Carlos Del Castillo Nieto, Barcelona (ES); Elisabet De Ramon Amat, Barcelona (ES)

(73) Assignee: Vita-Invest S.A., Sant Joan Despi (ES)

( * ) Notice: Subject to any disclaimer, the term of this patent is extended or adjusted under 35 U.S.C. 154(b) by 491 days.

(21) Appl. No.: 10/130,576

(22) PCT Filed: Nov. 15, 2000

(86) PCT No.: PCT/ES00/00432

§ 371 (c)(1),
(2), (4) Date: May 17, 2002

(87) PCT Pub. No.: WO01/36416

PCT Pub. Date: May 25, 2001

(30) Foreign Application Priority Data

Nov. 18, 1999 (ES) .................................... 9902533

(51) Int. Cl.
*C07D 417/12* (2006.01)
*A61K 31/506* (2006.01)

(52) U.S. Cl. .............................. 514/263.2; 514/263.23; 514/266.2; 514/256; 514/269; 514/274; 514/275; 544/277; 544/293; 544/311; 544/312; 544/317; 544/319; 544/321; 544/323; 544/6

(58) Field of Classification Search ................ 544/277, 544/293, 311, 312, 317, 319, 321, 323, 326; 514/263.2, 263.23, 266.2, 256, 269, 274, 514/275

See application file for complete search history.

(56) References Cited

U.S. PATENT DOCUMENTS 5,002,953 A    3/1991   Hindley ...................... 514/275

FOREIGN PATENT DOCUMENTS

EP      0193256      9/1986
WO      9207838      5/1992

OTHER PUBLICATIONS

Cantello, B.C.C., et al. "I[omega-(Heterocyclylamino)alkoxy]-2,4-thiazolidines as Potent Antihyperglycemic Agents" J. Med Chem, 1994, 37, 3977-3985 XP002901546.
Hulin, B, et al., "The Glitazone Family of Antidiabetic Agents", Current Pharmaceutical Design, 1996, 2, 85-102 XP002901547.

*Primary Examiner*—Deepak Rao
(74) *Attorney, Agent, or Firm*—Steinberg & Raskin, P.C.

(57) ABSTRACT

The present invention refers to compounds of the general formula (I), to their possible pharmaceutically acceptable salts and tautomeric forms. The present invention also refers to a process for their production and to their use as antidiabetic and *hypoglycemic agents, alone or in combination with other antidiabetic agents, such as sulfonilureas or biguanides, as well as for the treatment of complications associated to the resistance to the insulin, such as hypertension, hyperuricemia or other cardiovascular, metabolic, endocrine conditions, or other conditions related with diabetes.

11 Claims, No Drawings

THIAZOLIDINEDIONE DERIVATIVES AS ANTIDIABETIC AGENTS

This application is a 371 of PCT/SE00/00432 filed Nov. 15, 2000.

FIELD OF THE INVENTION

The present invention refers to new compounds that display a high hypoglycemic activity and, therefore, they are potentially useful in the treatment and/or prevention of diabetes and/or other alterations or complications characteristic of diabetes, such as hyperglycemia or hyperlipidemia.

BACKGROUND OF THE INVENTION

Diabetes mellitus encompasses a group of syndromes whose main characteristic feature is the high blood-glucose levels, or hyperglycemia. This gives rise to a long-term series of vascular-type complications such as nephropathy, retinopathy, and neuropathy.

Two diabetes types are distinguished. The one known as type-I diabetes (IDDM), caused by the deficiency in the secretion of insulin, the regulating hormone of glucose in blood, and the type-II diabetes (NIDDM) that is characterized mainly by a resistance to the regulating effect of insulin, this latter type being so much or even more important than the first one.

The current treatments against type II diabetes, with sulfonylureas and biguanides, are far from being ideal. Sulfonylureas can induce hypoglycemia and biguanides can cause lactic acidosis.

In the last years, thiazolidinedione derivatives with hypoglycemic activity have been described and, therefore, with application in the treatment of diabetes, mainly of the so-called "type II diabetes". The general structure of these compounds is:

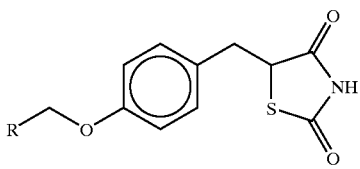

wherein R is a radical generally of aromatic or heteroaromatic type, and it can be linked or not to a N-type heteroatom.

A good review of this subject matter has been published by B. Hulin et al. (Current Pharmaceutical Design (1996), 2, 85–102).

As initial reference of this kind of structures the article of T. Sohda et al. (Chem. Pharm. Bull., 30 (10), 3580–3600 (1982)) may be taken into consideration. In this paper, the authors describe the synthesis of thiazolidinedione structures and, concretely, that of Ciglitazone, true starting point in the research of thiazolidinediones as hypoglycemic agents, also well-known as glitazones.

Several modifications have been made around the structure of these glitazones.

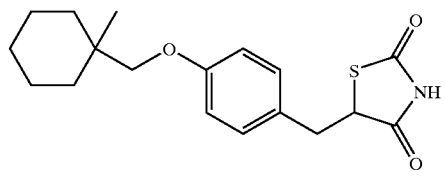

Ciglitazone

Modifications have been introduced in the lipophyllic moiety of the Ciglitazone structure, which has lead to the synthesis of new such compounds as Troglitazone (EP139421), Rosiglitazone (EP306228), Pioglitazone (EP193256).

Furthermore, modifications on the ether function have been disclosed (D. A. Clark et al., J. Med. Chem., 1991, 34, 319–325; R. L. Dow et al., J. Med. Chem., 1991, 34, 1538–1544; B. Hulin et al., J. Med. Chem. 1992, 35, 1853–1864), in which this function is built-in in a cycle fused with the aromatic ring, such as it happens in Englitazone (EP207605B):

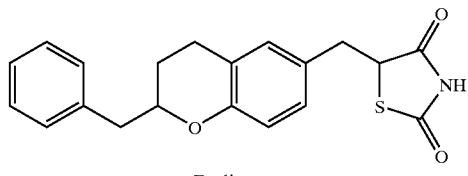

Englitazone

Surprisingly, the authors of the present invention have found new thiazolidindiones that show very good hypoglycemic properties.

DESCRIPTION OF THE INVENTION

The present invention refers to compounds of the general formula (I):

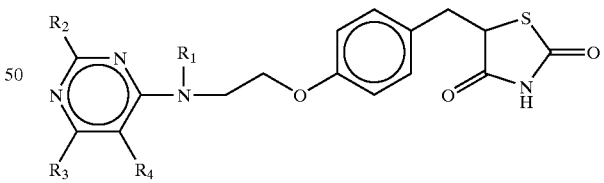

wherein $R_1$ is: H or $C_1$–$C_6$ alkyl;

$R_2$: H, $C_1$–$C_6$ alkyl, halogen (F, Cl, Br, I), $OR_5$, $SR_5$, $NR_5R_6$, $NO_2$, or phenyl;

$R_3$: H, $C_1$–$C_6$ alkyl, halogen (F, Cl, Br, I), $OR_5$, $SR_5$, $NR_5R_6$, $NO_2$, or phenyl;

$R_4$: H, $C_1$–$C_6$ alkyl, halogen (F, Cl, Br, I), $OR_5$, $NR_5R_6$, phenyl, or $R_3$ and $R_4$ when taken together, are —CH=CH—CH=CH—

$$-\text{N}=\text{C}-\text{N}- \quad \text{or} \quad -\text{N}-\text{C}=\text{N}-$$
$$\qquad\quad \underset{R_7}{|}\ \underset{R_8}{|} \qquad\qquad\quad \underset{R_8}{|}\ \underset{R_7}{|}$$

forming a fused ring on the pyrimidine ring.

$R_5$, $R_6$ are independent to each other, and they may be H or $C_1$–$C_6$ alkyl, $R_7$: H or $NH_2$, $R_8$: H, $C_1$–$C_6$ alkyl, to their possible pharmaceutically acceptable salts and tautomeric forms. The present invention also refers to a process for their production and to their use as antidiabetic and hypoglycemic agents, alone or in combination with other antidiabetic agents, such as sulfonilureas or biguanides, as well as for the treatment of complications associated to the resistance to the insulin, such as hypertension, hyperuricemia or other cardiovascular, metabolic and endocrine conditions, etc.

The preferred compounds of the present invention are those in which:

$R_1$: $CH_3$;

$R_2$: H, $OR_5$, $NR_5R_6$;

$R_3$: H, halogen (F, Cl, Br, I), $OR_5$;

$R_4$: H or $R_3$, $R_4$ when taken together, are $$-\text{N}-\text{C}=\text{N}- \quad \text{or} \quad -\text{N}=\text{C}-\text{N}-$$
$$\quad \underset{R_8}{|}\ \underset{R_7}{|} \qquad\qquad\qquad \underset{R_7}{|}\ \underset{R_8}{|}$$

wherein $R_7$ and $R_8$ are as previously defined.

Specially, the preferred compounds of the present invention are:

5-{4-[2-(Methylpyrimidin-4-yl-amino)-ethoxy]-benzyl}-thiazolidine-2,4-dione 5-(4-{2-[(6-Chloropyrimidin-4-yl)-methylamino]-ethoxy}-benzyl)-thiazolidine-2,4-dione 5-(4-{2-[(2-Amino-6-chloropyrimidin-4-yl)-methylamino]-ethoxy}-benzyl)-thiazolidine-2,4-dione 5-(4-{2-[(2,6-Dimethoxypyrimidin-4-yl)-methylamino]-ethoxy}-benzyl)-thiazolidine-2,4-dione 5-(4-{2-[Methyl-(7H-purin-6-yl)-amino]-ethoxy}-benzyl)-thiazolidine-2,4-dione 5-(4-{2-[Methyl-(9-methyl-9H-purin-6-yl)-amino]-ethoxy}-benzyl)-thiazolidine-2,4-dione 5-(4-{2-[(6-Methoxypyrimidin-4-yl)-methylamino]-ethoxy}-benzyl)-thiazolidine-2,4-dione 5-(4-{2-[(6-Hydroxypyrimidin-4-yl)-methylamino]-ethoxy}-benzyl)-thiazolidine-2,4-dione The compounds of the general formula (I) may be obtained via the following procedures:

Method A.

This method consists in reacting a compound of the formula (II), obtained as described in Barrie C. C. Cantello et al., *J. Med. Chem.*, (1994), 37, 3977–85, with a pyrimidine of the general formula (III), where $R_1$, $R_2$, $R_3$ and $R_4$ have the same meaning as for the compounds of the general formula (I),

SCHEMA I wherein X is a leaving group, such as a halogen group, specially Cl or Br.

The reaction is carried out in an inert medium at a temperature ranging from 10 to 120° C. As inert medium, toluene, DMF, etc. are preferably used.

Method B.—

This method consists in following the procedure described in the schema (II) below:

SCHEMA II

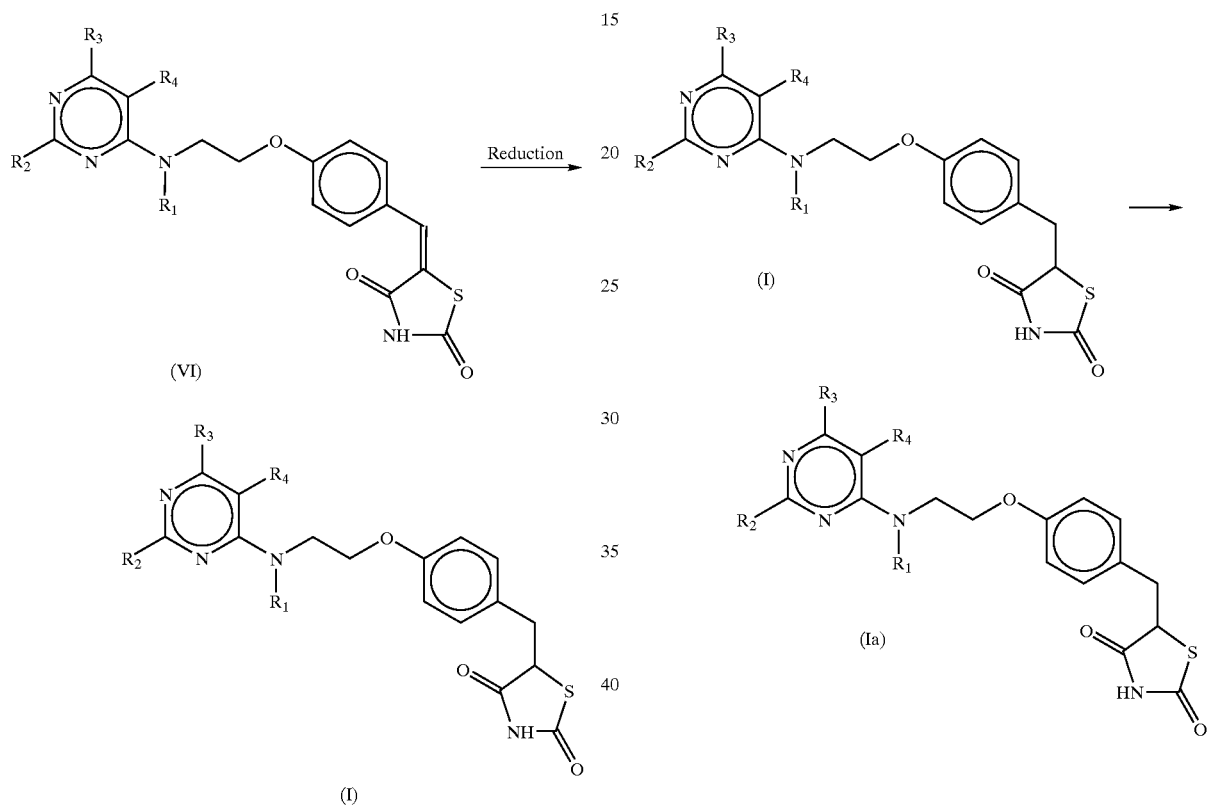

wherein the pyrimidine (III) is reacted with N-alkylaminoethanol ($R_1 = C_1-C_6$ alkyl) or with ethanolamine ($R_1 = H$), in the presence or the absence of a solvent, to a temperature between 10° C. and 120° C., to yield a compound of the formula (IV).

Compounds of the general formula (IV) are reacted with p-fluorobenzaldehyde in an inert solvent and in the presence of an equivalent of sodium borohydride. The reaction is carried out at temperatures between 0° C. and 120° C. In this way, compounds of the general formula V are obtained, which are reacted with 2,4-thiazolidinedione in toluene, heating to reflux, using piperidine acetate in catalytic amounts, while separating the water that is formed in the reaction with a Dean-Stark apparatus. In this way, compounds of the general formula (VI) are obtained.

The compounds of the general formula (VI) are subjected to a reduction process to obtain compounds of the general formula (I). This reduction reaction may be carried out with sodium borohydride, with metals in the presence or not of a proton donor, by enzymatic reduction or by catalytic hydrogenation.

Preferably, the reduction is carried out by means of a catalytic hydrogenation or by using a solution of sodium borohydride in water alkalinized with sodium hydroxide, and adding this solution onto a solution of the compound of the general formula (VI) in THF-DMF in the presence of catalytic amounts of cobalt chloride and dimethylglyoxime.

Method C.—

This method consists in reacting a compound of the general formula (I), to obtain a compound of the general formula (Ia), in which one of the substituents $R_2$, $R_3$ or $R_4$ is different from those of the starting compound.

EXPERIMENTAL PART

Method A.—

Example No. 1

5-(4-{2-[(6-chloro-2,5-diphenylpyrimidin-4-yl)-methyl-amino]-ethoxy}-thiazolidine-2,4-dione

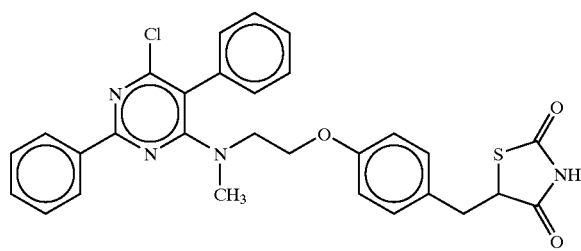

0.57 g (1.89 mmol) 4,6-dichloro-2,5-diphenylpyrimidine and 0.53 g (1.89 mmol) 5-[4-(2-methylamino-ethoxy)-benzyl]-thiazolidine-2,4-dione in 30 ml DMF are heated at 80° C. for 1 h.

Once the reaction completed, (CCF 90/10/1 CH$_2$Cl$_2$/EtOH/NH$_4$OH), the mixture is poured onto 300 ml water and then extracted with 3×300 ml ethyl acetate.

The organic phase is dried and concentrated. The residue is chromatographed on silica gel. Eluting with 95/5 CH$_2$—Cl$_2$/EtOH 0.4 g of a white solid is obtained (Yield 40%).

$^1$H-NMR (DMSO-d$_6$): 12.00 (br. s, 1H, NH); 8.36–8.32 (m, 2H); 7.60–7.30 (m, 8H); 7.12 (d, 2H); 6.82 (d, 2H); 4.82–4.76 (m, 1H); 4.17 (t, 2H); 3.83 (t, 2H); 3.24 (dd, 1H); 3.00 (dd, 1H); 2.74 (s, 3H, NCH$_3$)

Following the same procedure the following compounds have been obtained:

Example No. 2

5-(4-{2-[Methyl-(2-methylsulfanil-pyrimidin-4-yl)-amino]-ethoxy}-benzyl)-thiazolidine-2,4-dione

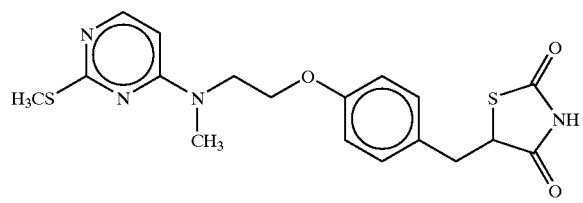

Starting from 1.15 g (8.3 mmol) 4-chloro-2-methylthiopyrimidine, 1.56 g of a solid is obtained (Yield 54%).

$^1$H-NMR (DMSO-d$_6$): 12.00 (br. s, 1H, NH); 8.01 (d, 1H); 7.08 (d, 2H); 6.86 (d, 2H); 6.42 (d, 2H); 4.84 (dd, 1H); 4.18 (t, 2H); 3.84 (br. s, 2H); 3.36 (dd, 1H); 3.10 (S, 3H, SCH$_3$) 3.04 (dd, 2H); 2.00–2.38 (s, 3H, NCH$_3$)

Example No. 3

5-(4-{2-[(2-amino-6-chloropyrimidin-4-yl)-methyl-amino]-ethoxy}-benzyl)-thiazolidine-2,4-dione

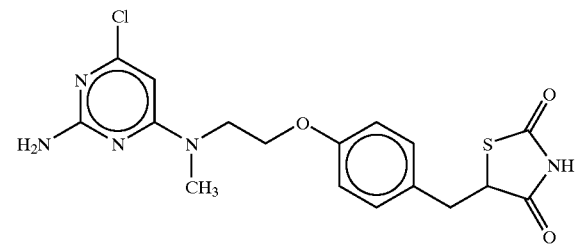

Starting from 1.18 g (7.2 mmol) 2-amino-4,6-dichloropyrimidine, 1.8 g of a solid is obtained (Yield 62%).

$^1$H-NMR (DMSO-d$_6$) 12.00 (br. s, 1H, NH); 7.19 (d, 2H); 6.86 (d, 2H); 6.48 (s, 2H, NH$_2$); 6.00 (s, 1H); 4.82 (dd, 1H); 4.10 (t, 2H); 3.84 (br. s, 2H); 3.36 (dd, 1H); 3.05 (dd, 1H); 3.04 (t, 3H, NCH$_3$).

Example No. 4

5-(4-{2-{(2,6-Dimethoxypyrimidin-4-yl)-methyl-amino]-ethoxy}-benzyl)-thiazolidine-2,4-dione

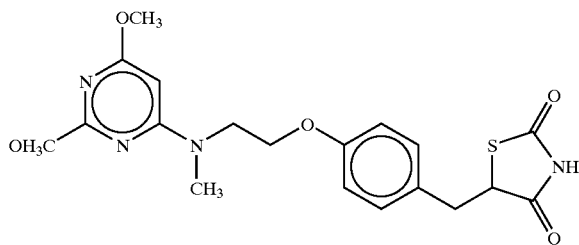

Starting from 0.94 g (5.3 mmol) 6-chloro-2,4-dimethoxypyrimidine, 0.84 g of a solid is obtained (Yield 38%).

H$^1$-NMR (DMSO-d$_6$): 12.00 (br. s, 1H, NH); 7.18 (d, 2H); 6.84 (d, 2H); 5.80 (s, 1H); 4.84 (dd, 1H) 4.16 (t, 2H); 3.90 (t, 2H); 3.78 (s, 3H, OCH$_3$); 3.76 (s, 3H, OCH$_3$); 3.36 (dd, 1H); 3.05 (dd, 1H); 3.04 (s, 3H, NCH$_3$).

Example No. 5

5-(4-{2-[(5-amino-6-chloropyrimidin-4-yl)-methyl-amino]-ethoxy}-benzyl)-thiazolidine-2,4-dione

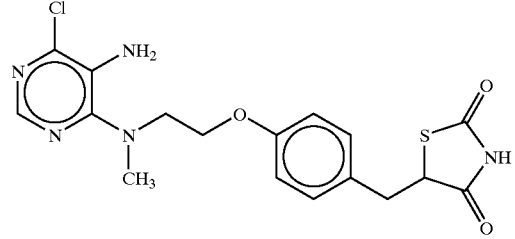

Starting from 0.99 (5.3 mmol) 5-amino-4-dichloropyrimidine, 1.1 g of a yellow solid is obtained.
$^1$H-NMR (DMSO-d$_6$): 12.00 (br. s, 1H, NH); 7.95 (s, 1H) 7.18 (d, 2H); 6.84 (d, 2H); 5.21 (br. s, 2H, NH$_2$); 4.84 (dd, 1H); 4.11 (t, 2H); 3.64 (t, 2H); 3.30 (dd, 1H); 3.03 (dd, 1H); 2.96 (s, 3H).

Example No. 6

5-(4-{2-[(6-chloro-2-methylsulfanil-5-phenylpyrimidin-4-il)-methylamino]-ethoxy}-benzyl)-thiazolidine-2,4-dione

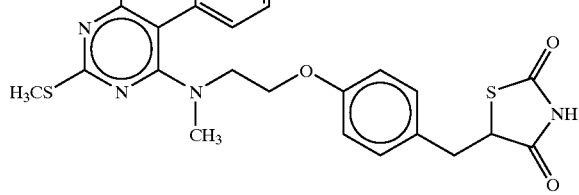

Starting from 1.5 g (5,3 mmol) of 4,6-dichloro-5-phenyl-2-methylthiopyridine 1.88 g of a solid is obtained (Yield 69%).

$^1$H-NMR (DMSO-d$_6$): 12.00 (br. s, 1H, NH); 7.46–7.38 (m, 3H); 7.30–7.26 (m, 2H); 7.18 (d, 2H); 6.82 (d, 2H); 4.82 (dd, 1H); 4.03 (t, 2H); 3.71 (t, 2H); 3.30 (dd, 1H); 3.02 (dd, 1H); 2.63 (s, 3H, NCH$_3$); 2.42 (s, 3H, SCH$_3$).

Example No. 7

5-(4-{2-[Methyl-(7H-purin-6-yl)-amino]-ethoxy}-benzyl)-thiazolidine-2,4-dione

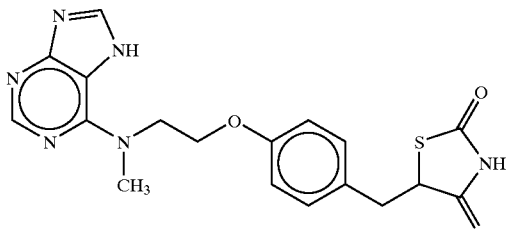

Starting from 0.83 g (5.3 mmol) 6-chloropurine, 0.6 g of a yellow solid is obtained (Yield 29%).

$^1$H-NMR (DMSO-d$_6$): 13.04 (br. s, 1H, NH); 12.00 (br. s, NH); 8.22 (s, 1H); 8.15 (s, 1H); 7.17 (d, 2H); 6.90 (d, 2H); 4.82 (dd, 1H); 4.40 (br. s, 2H); 4.14 (br. s, 2H); 3.44 (br. s, 3H); 3.30 (dd, 1H); 3.03 (dd, 1H).

Example No. 8

5-(4-{2-[(6-chloro-5-nitropyrimidin-4-yl)-methyl-amino]-ethoxy}-benzyl)-thiazolidine-2,4-dione

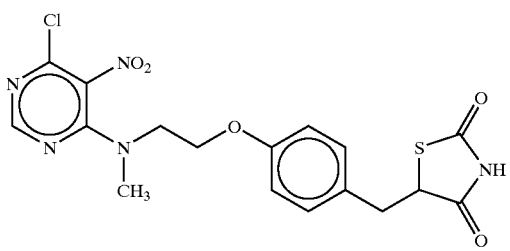

Starting from 1.04 g (5.3 mmol) 4,6-dicloro-5-nitropyridine, 0.3 g of the title compound is obtained (Yield 13%).

$^1$H-NMR (DMSO-d$_6$): 12.00 (br. s, 1H, NH); 8.54 (S, 1H); 7.18 (d, 2H); 6.83 (d, 2H); 4.79 (dd, 1H); 4.23 (t, 2H); 4.08 (t, 2H); 3.30 (dd, 1H); 3.06 (s, 3H, NCH$_3$); 3.04 (dd, 1H).

Example No. 9

5-(4-{2-[(8-amino-7H-purin-6-yl)-methylamino]-ethoxy}-benzyl)-thiazolidine-2,4-dione

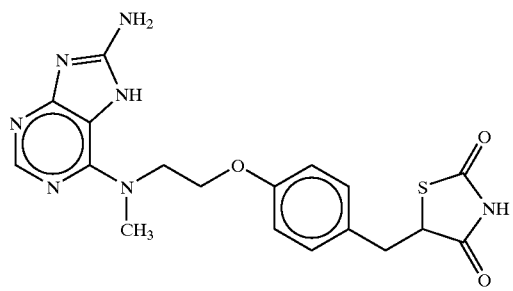

Starting from 1 g (9 mmol) 2-amino-6-chloropurine, 1.28 g of a yellow solid is obtained (Yield 54%).

$^1$H-NMR (DMSO-d$_6$): 12.10 (br. s, 1H, NH); 7.71 (s, 1H); 7.17 (d, 2H); 6.81 (d, 2H); 5.74 (br. s, 2H, NH$_2$); 4.81 (dd, 1H); 4.30 (br. s, 2H); 4.20 (br. s, 2H); 3.40 (br. s, 3H); 3.32 (dd, 1H); 3.05 (dd, 1H).

Example No. 10

5-[4-(2-Methyl-[9-(tetrahidropyran-2-yl)-9H-purin-6-yl]-amino}-ethoxy)-benzyl]-thiazolidine-2,4-dione

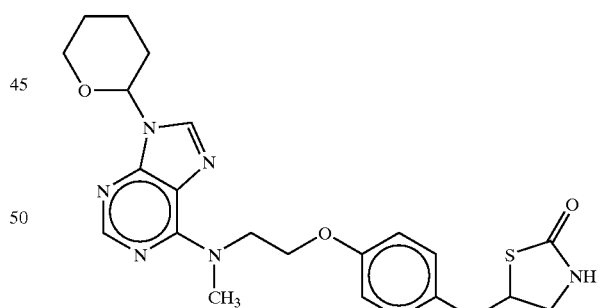

Starting from 1 g (4.5 mmol) 6-chloro-9-(tetrahydro-2-pyranil)purine, 1.3 g of a solid is obtained (Yield 65%).

$^1$H-NMR (DMSO-d$_6$): 12.00 (br. s, 1H, NH); 8.41 (s, 1H); 8.25 (s, 1H); 7.18 (d, 2H), 6.80 (d, 2H); 5.64 (d, 1H); 4.80 dd); 4.60–4.20 (br. s, 2H); 4.24 (br. s, 2H); 4.04 (d, 1H); 3.80–3.60 (m, 1H); 3.60–3.40 (br. s, 3H, NCH$_3$); 3.30 (dd, 1H); 3.03 (dd, 1H); 2.30–2.10 (m, 1H); 2.10–1.90 (m, 2H); 1.90–1.70 (m, 1H); 1.70–1.50 (m, 2H).

Example No. 11

5-[4-{2-[9-(3,4-Dihydroxy-5-hydroxymethyl-tetrahydrofuran-2-yl)-9H-purin-6-yl]-methylamino}-ethoxy)-benzyl]-thiazolidine-2,4-dione

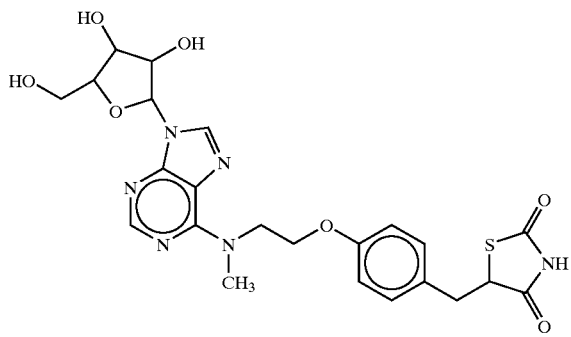

Starting from 1 g (3.5 mmol) 6-chloropurine-D-riboside, 1.2 g of a solid is obtained (Yield 65%).

$^1$H-NMR (DMSO-d$_6$): 12.00 (br. s, 1H, NH); 8.42 (s, 1H); 8.23 (s, 1H); 7.18 (d, 2H); 6.80 (d, 2H); 5.95 (d, 1H); 5.46 (d, 1H, OH); 5.37 (t, 1H, OH); 5.21 (d, 1H, OH); 4.86 (dd, 1H); 4.62 (t, 2H); 4.25 (br. s, 2H); 4.21–4.17 (m, 2H); 3.98–3.95 (m, 1H); 3.75–3.25 (m, 6H); 3.05 (dd, 1H).

Example No. 12

5-(4-{2-[Methyl-(9-methyl-9H-purin-6-yl)-amino]-ethoxy}-benzyl)-thiazolidine-2,4-dione

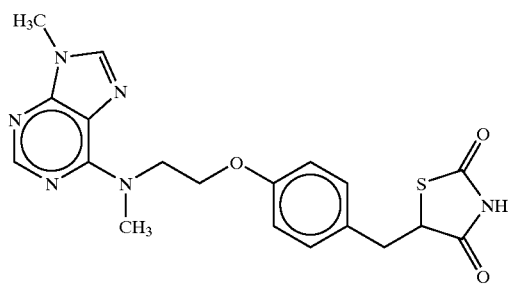

Starting from 1 g (6 mmol) 6-chloro-9-methylpurine, obtained by methylation of 6-chloropurine with methyl iodide in acetone and in the presence of potassium carbonate, 1.02 g of a yellow solid is obtained (Yield 41%).

$^1$H-NMR (DMSO-d$_6$): 12.00 (br. s, 1H, NH); 8.24 (S, 1H); 8.17 (s, 1H); 7.16 (d, 2H); 6.84 (d, 2H); 4.82 (dd, 1H); 4.60–4.10 (br. s, 2H); 4.30–4.20 (br. s, 2H); 3.75 (br. s, 3H, NCH$_3$); 3.603.20 (br. s, 3H, NCH$_3$); 3.30 (dd, 1H); 3.03 (dd, 1H).

Example No. 13

5-(4-{2-[Methyl-(7-methyl-7H-purin-6-yl)-amino]-ethoxy}-benzyl)-thiazolidine-2,4-dione

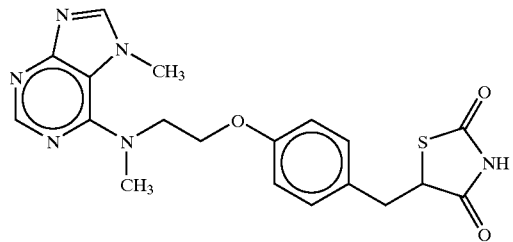

Starting from 0.5 g (3 mmol) 6-chloro-7-methylpurine, obtained as a byproduct in the alkylation of 6-chloropurine with methyl iodide, 0.38 g of an orange-colored solid are obtained (Yield 31%).

$^1$H-NMR (DMSO-d$_6$): 12.00 (br. s, 1H, NH); 8.40 (s, 1H); 8.35 (s, 1H); 7.12 (d, 2H); 6.81 (d, 2H); 4.69 (dd, 1H); 4.25 (t, 2H); 3.97 (s, 3H, NCH$_3$); 3.90 (t, 2H); 3.30 (dd, 1H); 3.20 (S, 3H, NCH$_3$); 2.95 (dd, 1H).

Example No. 14

5-(4-{2-[(6-chloropyrimidin-4-yl)-methylamino]-ethoxy}-benzyl)-thiazolidine-2,4-dione

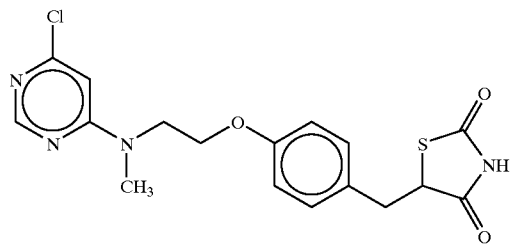

Starting from 1.1 g (7.4 mmol) 4,6-dichloropyrimidine, 2 g of a white solid is obtained (Yield 72%).

$^1$H-NMR (DMSO-d$_6$): 12.00 (br. s, 1H, NH); 8.19 (s, 1H); 7.18 (d, 2H); 6.85 (s, 1H); 6.83 (d, 2H); 4.82 (dd, 1H); 4.17 (t, 2H); 4.03–3.82 (br. s, 2H); 3.30 (dd, 1H); 3.14 (s, 3H, NCH$_3$); 3.05 (dd, 1H).

Example No. 15

5-(4-{2-[(2-amino-6-methylpyrimidin-4-yl)-methylamino]-ethoxy}-benzyl)-thiazolidine-2,4-dione

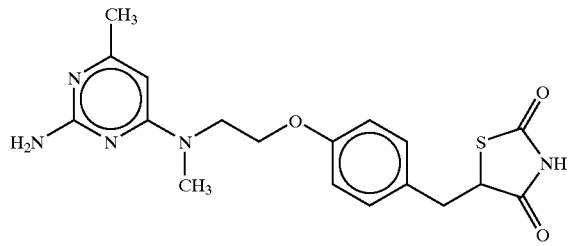

Starting from 0.8 g (5.3 mmol) 2-amino-4-chloro-6-methylpyrimidine, 1.2 g of a white solid is obtained (Yield 58%).

$^1$H-NMR (DMSO-d$_6$): 12.00 (br. s, 1H, NH); 7.16 (d, 2H); 6.87 (d, 2H); 6.08 (br. s, 2H, NH$_2$); 5.84 (s, 1H); 4.71 (dd, 1H); 4.10 (t, 2H); 3.85 (t, 2H); 3.31 (dd, 1H); 3.05 3H, NCH$_3$); 2.98 (dd, 1H); 2.10 (s, 3H, CH$_3$).

Example No. 16

5-(4-{2-[Methyl-(2-phenylquinazolin-4-yl)-amino]-ethoxy}-benzyl)-thiazolidine-2,4-dione

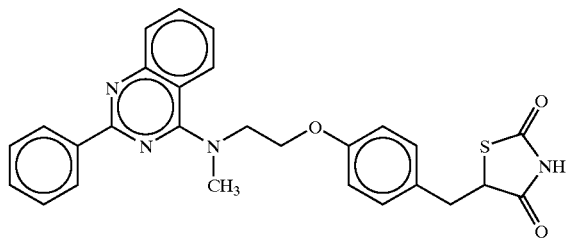

Starting from 1.3 g (5.3 mmol) 4-chloro-2-phenylquinazoline, 1.6 g of a yellow solid is obtained (Yield 62%).

$^1$H-NMR (DMSO-d$_6$): 12.00 (br. s, 1H, NH); 8.50–8.42 (m, 2H); 8.24 (d, 1H); 7.84–7.76 (m, 2H); 7.52–7.42 (m, 4H); 7.16 (d, 2H); 6.84 (d, 2H); 4.84 (dd, 1H); 4.42 (t, 2H); 4.24 (t, 2H); 3.58 (s, 3H, NCH$_3$), 3.30 (dd, 1H); 3.04 (dd, 1H).

Example No. 17

5-(4-{2-[(6-Methoxypyrimidin-4-yl)-methylamino]-ethoxy}-benzyl)-thiazolidine-2,4-dione

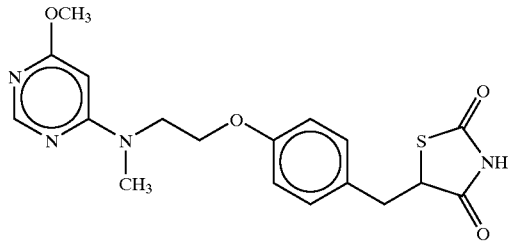

A starting mixture consisting of 2.9 g (0.02 mol) 4-chloromethoxypyrimidine and 5.6 g (0.02 mol) 5-[4-(2-methylaminoethoxy)-benzyl]-thiazolidine-2,4-dione in 60 ml DMF and in the presence of 17 g NaHCO$_3$ is heated at 100° C. for 24 h. Once the reaction completed, the mixture is poured onto 600 ml water and it is extracted with 4×200 ml AcOEt.

The extracts are dried and concentrated, and the residue is chromatographed on silica gel. By elution with 95/5 CH$_2$Cl$_2$/EtOH 2.5 g of a white solid is obtained.

Yield 32%

$^1$H-NMR (DMSO-d$_6$): 12.00 (br. s, 1H, NH); 8.22 (s, 1H); 7.18 (d, 2H); 6.84 (d, 2H); 5.92 (s, 1H); 4.84 (dd, 1H); 4.10 (t, 2H); 3.90 (t, 2H); 3.82 (s, OCH$_3$); 3.32 (dd, 1H); 3.04 (s, NCH$_3$); 3.02 (dd, 1H).

Example No. 18

5-(4-{2-[(2-amino-6-methoxypyrimidin-4-yl)-methylamino]ethoxy}-benzyl)-thiazolidine-2,4-dione

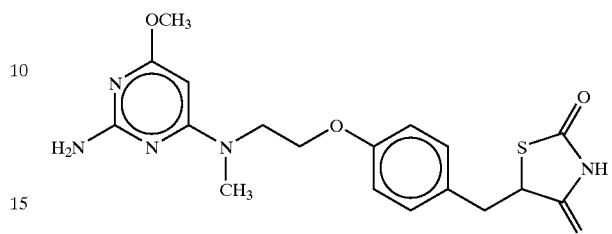

Starting from of 1.5 g (0.01 mol) 2-amino-4-chloromethoxypyrimidine and following the procedure described in the previous Example, 1.1 g of the title compound is obtained.

Yield 27%

$^1$H-NMR (DMSO-d$_6$): 12.00 (br. s, 1H, NH); 7.18 (d, 2H); 6.84 (d, 2H); 6.04 (s, 2H, NH$_2$); 5.21 (s, 1H); 4.84 (dd, 1H); 4.08 (t, 2H); 3.82 (t, 2H); 3.74 (s, 3H, OCH$_3$); 3.32 (dd, 1H); 3.08 (dd, 1H); 3.00 (s, 3H, NCH$_3$).

Example No. 19

5-{4-[2-(6-chloro-2-methoxypyrimidin-4-yl)-amino)-ethoxy]-benzyl}-thiazolidine-2,4-dione

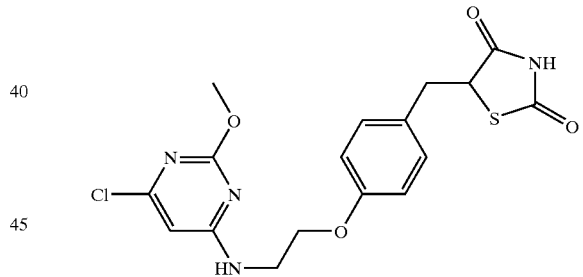

A starting mixture consisting of 1.8 g (0.01 mmol) 2-methoxy-4,6-dichloropyrimidine, 2.7 g (0.01 mol) 5-[4-(2-aminoethoxy)-benzyl]-thiazolidine-2,4-dione hydrochloride and 1.68 g (0.02 mol) sodium bicarbonate was heated to 120° C. in 50 ml dimethylformamide for 2 hours. Once the reaction completed, the mixture is cooled and then poured onto 500 ml of water, whereby a solid precipitates, which is then filtered.

The filtration liquors are extracted with 3×100 ml AcOEt. The extracts are dried with sodium sulfate, filtered and concentrated. The residue is pooled together with the previously filtrated solid and stirred in 50 ml methanol. The undissolved solid is then filtered to give 3.4 g (Yield: 84%) of a entirely pure product.

$^1$H-NMR (DMSO-d$_6$): 12.00 (br. s, 1H, NH); 8.05 (br. s, 1H, NH); 7.21 (d, 2H); 6.90 (d, 2H); 6.24 (s, 1H); 4.86 (dd, 1H); 4.12 (t, 2H); 3.84 (s, 3H); 3.68 (br. s, 2H); 3.38 (dd, 1H); 3.05 (dd, 1H).

Method B.—

Example No. 20

5-{4-[2-(Methylpyrimidin-4-yl-amino)ethoxy]benzyl}-thiazolidine-2,4-dione

20.1—Synthesis of 2-[(6-chloropyrimidin-4-yl)-methylamino]-ethanol

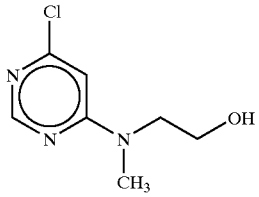

To a solution of 14.8 g (0.1 mmol) 2,4-dichloropyrimidine in 120 ml ethanol and 20 ml water, cooled to 0° C., 11.3 g (0.15 mol) 2-(N-methylamino)ethanol is added. The resulting mixture is stirred at room temperature for ½ h., then concentrated to dryness and finally partitioned between $CH_2Cl_2$ and a $NaHCO_3$ saturated solution.

The organic phase is dried and concentrated. The residue is stirred in 20 ml $CH_2Cl_2$, and then the precipitated white solid is filtered. 7.7 g is obtained. From the filtration liquor a further 5.8 g of pure product is recovered by means of a silica gel column, eluting with 1/1 heptane/AcOEt.

Yield 72%

$^1$H-NMR (CDCl$_3$): 8.30 (s, 1H); 6.45 (1, 1H); 3.89 (t, 2H); 3.78 (t, 2H); 3.10 (s, 3H, NCH$_3$).

20.2—Synthesis of 2-(methylpyrimidin-4-yl-amino)-ethanol

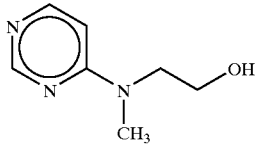

To 9.4 g (50 mmol) 2-[(6-chloropyrimidin-4-yl)-methylamino)ethanol in 50 ml ethanol and 10 ml water, 1 g of a 10% Pd/C paste is added and the resulting mixture is subjected to hydrogenation at a pressure of 60 atmospheres and at room temperature for 8 h.

The solution is filtered on decalite. The filtrate is concentrated to dryness and then partitioned between a saturated sodium bicarbonate solution (100 ml) and 100 ml $CH_2Cl_2$. The aqueous phase is extracted with an additional 2×100 ml $CH_2Cl_2$ and the extracts are pooled together with the previous ones.

The extracts are dried, then concentrated, and the residue is purified by column chromatography using silica gel as a support, and eluting with 9/1 $CH_2Cl_2$/EtOH.

4.1 g of a colorless oil is obtained (Yield 54%).

$^1$H-NMR (CDCl$_3$): 8.48 (s, 1H); 8.09 (d, 1H); 6.43 (d, 1H); 4.90–4.80 (br. s, 1H, OH); 3.83 (t, 2H); 3.74 (t, 2H); 3.10 (s, 3H, NCH$_3$).

20.3—Synthesis of 4-[2-(methylpyrimidin-4-yl-amino)-ethoxy]-benzaldehyde

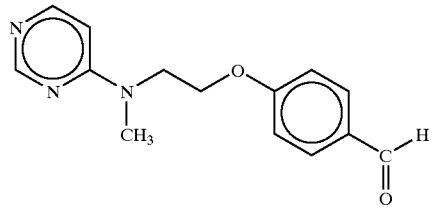

Onto 30 ml DMF 0.88 g (22 mmol) sodium hydride (60% in mineral oil) and 2.9 g (19 mmol) 2-[6-chloropyrimidin-4-yl)-methylamino]-ethanol are added. The mixture is stirred at room temperature for ½ h. A 2.6 g portion (21 mmol) of p-fluorobenzaldehyde is then added thereto and the resulting mixture is heated at 50° C. for 15 minutes.

The reaction mixture is poured onto 300 ml water and then extracted with 3×100 ml AcOEt. The organic phase is dried, filtered and concentrated, and the residue chromatographed on silica gel. Eluting with 1/1 Heptane/AcOEt 2.5 g of the title compound is obtained (Yield 51%).

$^1$NMR (CDCl$_3$): 9.90 (s, 1H, CHO); 8.62 (s, 1H); 8.28–8.18 (br. s, 1H) 7.83 (d, 2H); 7.00 (d, 2H); 6.51 (d, 1H); 4.30 (t, 2H); 4.08 (t, 2H); 3.21 (s, 3H, NCH$_3$).

20.4—Synthesis of 5-{4-[2-(methylpyrimidin-4-yl-amino)-ethoxy]-benzylidene}-thiazolidine-2,4-dione

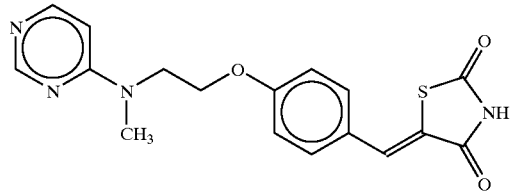

To 2.3 g (8 mmol) 4-[2-(methylpyrimidin-4-yl-amino)-ethoxy]-benzaldehyde in 40 ml toluene 1.06 g (8.9 mmol) of 90% 2,4-thiazolidinedione is added. Then, 0.06 ml (0.78 mmol) piperidine and 0.044 ml (0.78 mmol) acetic acid are further added thereto. The mixture is heated to reflux for 5 h while separating the water that is formed with a Dean-Stark apparatus.

The reaction mixture is allowed to cool and the solid precipitate is then filtered off. 2.5 g of product is obtained (yield 88%)

$^1$H-RMN (DMSO-d$_6$): 8.50 (s, 1H); 8.15 (d, 1H); 7.70 (s, 1H); 7.51 (d, 2H); 7.07 (d, 2H); 6.70 (d, 1H); 4.25 (t, 2H); 3.96 (t, 2H); 3.10 (s, 3H, NCH$_3$).

20.5—Synthesis of 5-{4-[2-(methylpyrimidin-4-yl-amino)-ethoxy]-benzyl}-thiazolidine-2,4-dione

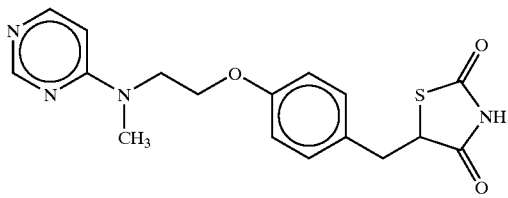

To a stirred solution of 7.5 mg (0.025 mmol) cobalt chloride hexahydrate and 116 mg (1 mmol) dimethylglyoxime in 40 ml of water, 4 drops 1N NaOH are added, followed by the addition of 0.57 g (15 mmol) sodium borohydride.

Onto this solution, cooled to 0° C., 1.8 g (5 mmol) 5-{4-[2-(methylpyrimidin-4-yl-amino)-ethoxy]-benzylidene}-thiazolidine-2,4-dione dissolved in 30 ml of DMF is added.

The reaction mixture is kept at room temperature for 24 h and then poured onto 300 ml water, and the pH adjusted to 6–7 with acetic acid. The precipitated white solid is filtered off, treated with 100 ml MeOH, and heated to reflux. The MeOH solution is hot-filtered in order to remove any residual starting compound.

From the filtration-liquor, 1.5 g end product is obtained by crystallization (Yield 84%).

$^1$H-NMR (DMSO-$d_6$): 12.00 (br. s, 1H, NH); 8.48 (s, 1H); 8.17 (d, 1H); 7.14 (d, 2H); 6.84 (d, 2H); 6.70 (d, 1H); 4.82 (dd, 1H); 4.12 (t, 2H); 3.90 (t, 2H); 3.30 (dd, 1H); 3.10 (s, 3H, NCH$_3$); 3.03 (dd, 1H).

Method C.—

Example No. 21

5-(4-{2-[(6-Dimethylaminopyrimidin-4-yl)-methylamino]-ethoxy}-benzyl)-thiazolidine-2,4-dione

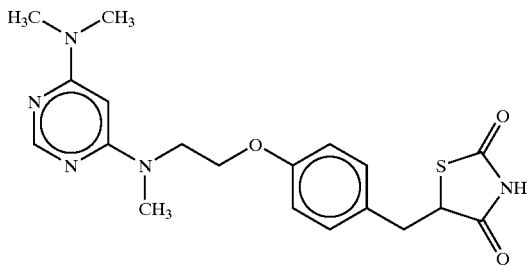

To 1 g (2.5 mmol) of the compound obtained in the Example No. 14 in 30 ml DMF, 0.21 g (2.5 mmol) NaHCO$_3$ and 1.8 ml (25 mmol) 60% dimethylamine in water are added.

The mixture is heated at 80° C. for 24 h, then concentrated to dryness and the residue partitioned between 100 ml water and 100 ml CH$_2$Cl$_2$. The organic phase is dried and concentrated. The residue is chromatographed on silica gel.

Eluting with 96/4 CH$_2$Cl$_2$/EtOH 0.5 g of the title compound is obtained.

$^1$H-NMR (DMSO-$d_6$): 12.00 (br. s, 1H); 8.06 (s, 1H); 7.18 (d, 2H); 6.86 (d, 2H); 5.50 (s, 1H); 4.84 (dd, 1H); 4.10 (t, 2H); 3.56 (t, 2H); 3.30 (dd, 1H); 3.04 (s, 3H, NCH$_3$); 3.02 (dd, 1H) 2.98 (s, 6H).

Example No. 22

5-(4-{2-[(6-Hydroxypyrimidin-4-yl)-methylamino]-ethoxy}-benzyl)-thiazolidine-2,4-dione

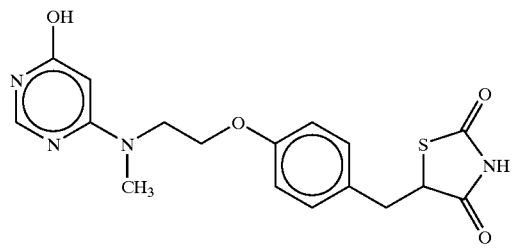

To 1.9 (5 mmol) of the compound obtained in the Example No. 17 in 40 ml acetic acid, 3.5 ml (20 mmol) of a hydrobromic acid solution in 33% acetic acid is added.

The reaction is heated at 80° C. for 4 h. Once the reaction completed, the mixture is poured onto water and the white solid which precipitates is filtered off and then stirred for 30 minutes in 50 ml EtOH. The resulting suspension is filtered again, and 1.2 g of a completely pure white solid is obtained. Yield 64%.

$^1$H-NMR (DMSO-$d_6$): 12.00 (br. s, 1H); 11.62 (br. s, 1H); 7.90 (s, 1H); 7.18 (d, 2H); 6.84 (d, 2H); 5.10 (s, 1H); 4.82 (dd, 1H); 4.10 (t, 2H); 3.86–3.80 (br. s, 2H); 3.32 (dd, 1H); 3.04 (dd, 1H); 2.97 (s, 3H, NCH$_3$).

Pharmacological Methods

The pharmacological effect of the compounds is assessed in genetically diabetic C57 BL male db/db 9–11 weeks old mice, as well as in control C57 BL db/+ animals of the same strain and age. The db/db mice show most of the metabolic alterations that appear in the type-2 diabetes, while the control animals do not develop the illness. In each experimental group, 8–10 animals are used, which are treated with different doses of the compounds: 1 mg/kg, 5 mg/kg, 10 mg/kg or 25 mg/kg orally during 5 consecutive days.

In the day 0 of the experiment, blood samples are collected in heparinized tubes by punction of the retroorbital vein. Plasma is separated and the levels of basal glucose and insulin are quantified.

After concluding the treatments, blood samples of each animal are collected again and plasmatic post-treatment glucose and insulin levels are quantified.

The determination of glucose is carried out by means of an enzymatic method that converts glucose into glucose 6-phosphate, a reaction coupled with the reduction of nicotinamide-dinucleotide phosphate (NADP) to NADPH by the action of glucose-6-P-dehydrogenase. The NADPH reduces the iodonitrotetrazolium, which is quantified spectrophotometrically. The absorbency at 520 nm is proportional to the concentration of glucose, ref: Randox GI, 2623 (Bergmeyer H. U., Bernt E., Schmidt F. H., Stork H. In Methods of Enzymatic Analysis, Academic Press: London and New York 1974, p. 1196).

The results are expressed as the reduction percent with regard to the basal levels determined before the beginning of the treatment.

The obtained results are shown in Table 1. As it can be seen from the Table, the compounds of the present invention attain a reduction of glucose levels higher than that achieved by the standard troglitazone), even with doses 100-fold lower.

TABLE 1

| Compound | Dose (mg/kg, p.o.) | % glucose reduction |
| --- | --- | --- |
| Troglitazone | 100 | 38 |
| Example 3 | 1 | 47 |
| Example 4 | 1 | 53 |
| Example 7 | 10 | 47 |
| Example 11 | 10 | 30 |
| Example 12 | 10 | 25 |
| Example 14 | 1 | 51 |
| Example 17 | 1 | 48 |
| Example 20 | 5 | 21 |
| Example 21 | 25 | 36 |
| Example 22 | 5 | 22 |

What is claimed is:

1. A compound of the general formula

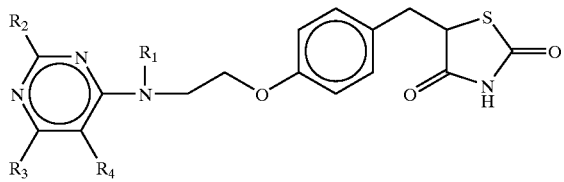

(I)

wherein:
$R_1$ is: H or $C_1$–$C_6$ alkyl,
$R_2$: H, $C_1$–$C_6$ alkyl, halogen (F, Cl, Br, I), $OR_5$, $SR_5$, $NR_5R_6$, $NO_2$, or phenyl,
$R_3$: H, $C_1$–$C_6$ alkyl, halogen (F, Cl, Br, I), $OR_5$, $SR_5$, $NR_5R_6$, $NO_2$, or phenyl,
$R_4$: H, $C_1$–$C_6$ alkyl, halogen (F, Cl, Br, I), $OR_5$, $NR_5R_6$, phenyl,
or $R_3$ and $R_4$, when taken together, are
—CH=CH—CH=CH—

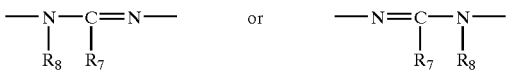

forming a fused ring on the pyrimidine ring
$R_5$, $R_6$: independently to each other, may be H or $C_1$–$C_6$ alkyl,
$R_7$: H or $NH_2$,

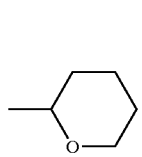 or 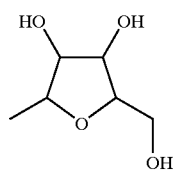

$R_8$: H, $C_1$–$C_6$ alkyl,
or a pharmaceutically acceptable salt or tautomeric form thereof.

2. A compound of the general formula (I) according to claim 1, wherein:
$R_1$: $CH_3$
$R_2$: H, $OR_5$, $NR_5R_6$
$R_3$: H, halogen (F, Cl, Br, I), $OR_5$
$R_4$: H
or $R_3$, $R_4$, when taken together, are

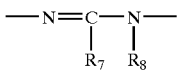

3. A compound according to claim 1, selected from the group consisting of:
5-{4-[2-(Methylpyrimidin-4-yl-amino]-ethoxy]-benzyl}-thiazolidine-2,4-dione,
5-{4-{2-[(6-Chloropyrimidin-4-yl)-methylamino]-ethoxy}-benzyl)-thiazolidine-2,4-dione,
5-(4-{2-[(2-Amino-6-chloropyrimidin-4-yl)-methylamino]-ethoxy}-benzyl)-thiazolidine-2,4-dione,
5-(4-{2-[(2,6-Dimethoxypyrimidin-4-yl)-methylamino]-ethoxy}-benzyl)-thiazolidine-2,4-dione,
5-(4-{2-[Methyl-(7H-purin-6-yl)-amino]-ethoxy}-benzyl)-thiazolidine-2,4-dione,
5-(4-{2-[Methyl-(9-methyl-9H-purin-6-yl)amino] ethoxy}-benzyl)thiazolidine-2,4-dione,
5-(4-{2-[(6-Methoxypyrimidin-4-yl)-methylamino]-ethoxy}-benzyl)-thiazolidine-2,4-dione and
5-(4-{2-[(6-Hydroxypyrimidin-4-yl)-methylamino]-ethoxy}-benzyl)-thiazolidine-2,4-dione.

4. A process for the preparation of a compound according to claim 1, wherein a compound of the general formula (III) is reacted with a compound of the formula (II):

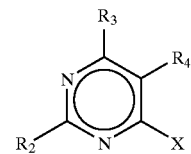

(III)

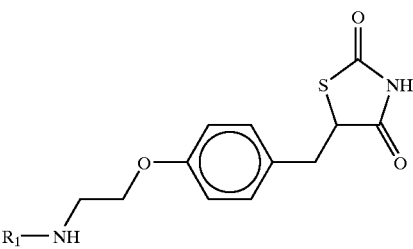

(II)

wherein X is a leaving group, in a inert medium at a temperature ranging from 10 to 120° C.

5. The process of claim 4, wherein said leaving group is a halogen.

6. The process of claim 5, wherein said halogen is chlorine or bromine.

7. A process for the preparation of a compound according to claim 1, which comprises the reduction of a compound of the formula (VI):

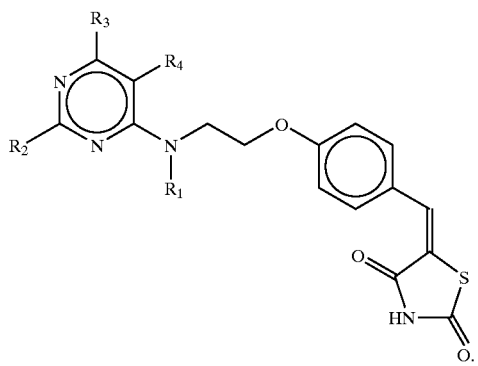

(VI)

8. A process according to claim 7, wherein said reduction reaction is carried out with sodium borohydride, with metals optionally in the presence of a proton-donor, by enzymatic reduction or by catalytic hydrogenation.

9. A pharmaceutical composition which comprises a compound of claim 1, and a pharmaceutically acceptable carrier.

10. The pharmaceutical composition according to claim 9, further, comprising one or more other antidiabetic agents.

11. The pharmaceutical composition of claim 10, wherein the antidiabetic agent is a sulfonylurea or a biguanide.

* * * * *